United States Patent [19]
Adams et al.

[11] 3,981,905
[45] Sept. 21, 1976

[54] 2-(SUBSTITUTED PHENYL) PROPIONIC ACIDS

[75] Inventors: Stewart Sanders Adams; Bernard John Armitage; John Stuart Nicholson; James Gordon Tantum, all of Nottingham, England

[73] Assignee: Boots Pure Drug Company Limited, Nottingham, England

[22] Filed: Nov. 13, 1973

[21] Appl. No.: 415,319

Related U.S. Application Data

[63] Continuation of Ser. No. 123,108, March 10, 1971, abandoned.

[30] Foreign Application Priority Data
Mar. 16, 1970  United Kingdom............. 12570/70

[52] U.S. Cl. .................. 260/473 R; 260/247.1 T; 260/307 F; 260/465 E; 260/465 F; 260/471 R; 260/518 A; 260/520 R; 260/544 N; 260/558 A; 260/559 D; 260/571; 260/576; 260/544 D; 260/592; 260/599; 260/613 R; 424/308; 424/309; 424/317; 424/324; 424/330; 424/341

[51] Int. Cl.$^2$............. C07C 65/14; C07C 101/447
[58] Field of Search........................ 260/520, 473 R

[56] References Cited
UNITED STATES PATENTS

| | | | |
|---|---|---|---|
| 3,385,886 | 5/1968 | Nicholson et al. ............. | 260/473 R |
| 3,600,437 | 8/1971 | Marshall ......................... | 260/473 R |
| 3,624,142 | 11/1971 | Shen et al. ...................... | 260/473 R |
| 3,649,679 | 3/1972 | Marshall ......................... | 260/473 R |

OTHER PUBLICATIONS

Julia et al., Bull. Soc. Chim. France, (1953), pp. 640–647, (Two Articles).
Burger, "Medicinal Chemistry," 3rd Ed., 64–72, (1970).

*Primary Examiner*—Robert Gerstl
*Attorney, Agent, or Firm*—Hammond & Littell

[57] ABSTRACT

2-(Substituted phenyl)propionic acids and salts, esters, amides and alcohols derived therefrom, said substituents being halogen atoms, useful an antiinflammatory agents, and their preparation.

6 Claims, No Drawings

2-(SUBSTITUTED PHENYL) PROPIONIC ACIDS

This is a continuation of Ser. No. 123,108, filed Mar. 10, 1971, and now abandoned.

This invention relates to novel 2-(substituted phenyl)propionic acids and salts, esters, amides and alcohols derived therefrom, which have been found to possess valuable biological properties.

According to one feature of the invention there are provided compounds of general formula I

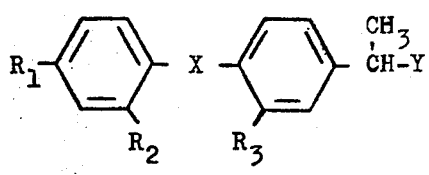

I in which

X is O or NH;

$R_1$ is halogen;

$R_2$ and $R_3$ are each selected from hydrogen and halogen, at least one being hydrogen;

Y is COOH, $CONH_2$ or $CH_2OH$; together with pharmaceutically acceptable esters, inorganic salts and organic salts of those compounds wherein Y is COOH.

Typical methods suitable for the preparation of the compounds of general formula I are as follows. Processes for the preparation of the stated starting materials and exact reaction conditions for the typical methods for the preparation of compounds of general formula I will be readily apparent to those skilled in the art from inherent knowledge, the prior art literature and the examples appended to this specification. As the methods are so-called "analogy processes" the descriptions have been kept brief and it is to be understood that any known procedures may be used to carry out the methods in addition to those procedures to which specific references are made.

In the following description the symbol Ro is used to represent

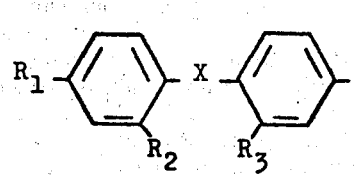

ACIDS

1. Hydrolysis of

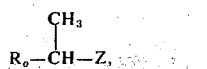

wherein Z is cyano, carbamoyl, N,N-disubstituted thiocarbamoyl, or $COOR_4$ in which $R_4$ is an ester-forming group, especially lower alkyl. The N,N-disubstituted thiocarbamoyl group is preferably derived from morpholine.

The hydrolysis may be carried out according to methods well-known in the art, for example by the use of acid or alkali in water, in an organic liquid reaction medium, or in a mixture thereof; a treatment temperature of 15°–150°C. is convenient. Preferably the hydrolysis is carried out by refluxing in the presence of an alkali metal hydroxide or of a mineral acid, and the organic liquid reaction medium is a lower alkanol.

The starting materials may be prepared, for example, from the substituted acetophenones $R_o$—CO—$CH_3$ by conventional means; other methods include the methods outlined below under the "Esters" and "Amides" headings below.

2. Decarboxylation of

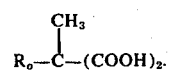

This may be carried out by heating the compound at about 200°C.

The starting materials may be conveniently prepared in conventional manner, for example by reacting an alkyl ester of the acid $R_o$—$CH_2$—COOH with an alkyl carbonate and an alkali metal alkoxide to yield an alkali metal derivative of a compound of formula $R_o$—CH—(COOalkyl)$_2$, methylating this and hydrolyzing the product.

3. Methylation of $R_o$—$CH_2$—COOH.

A metal (e.g. sodium) derivative of the acetic acid is used, prepared for example by reaction of the acid with an alkali metal amide (e.g. sodamide) in a suitable medium e.g. liquid ammonia. Conventional methylating agents may be used e.g. methyl iodide, dimethyl sulphate, and the like.

4. Oxidation of

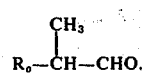

The oxidation may be carried out using any suitable oxidizing agent such as permanganates, chromic acid, dichromates, per acids, hydrogen peroxide, nitric acid, hypochlorites, silver oxide, or oxygen. A very convenient procedure involves oxidation in aqueous ethanol with alkali (e.g. an alkali metal hydroxide) and silver oxide.

The starting materials may be prepared by the methods described for related compounds in our British Pat. Specification No. 1,160,725.

5. Reductive cleavage of

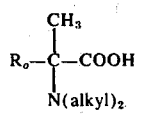

This may be achieved by conventional methods such as by catalytic hydrogenation e.g. using a palladium charcoal catalyst, or by treatment with sodium in liquid ammonia.

The starting materials may be prepared by the methods described for related compounds in our British Pat. Specification No. 1,167,192.

6. Hydrogenation of $$R_o-\overset{\overset{\displaystyle CH_2}{\|}}{C}-COOH.$$

Typical procedures include hydrogenation over a conventional catalyst such as, for example, palladium, palladium oxide or platinum in an inert solvent such as a lower alkanol, benzene, toluene, xylene, tetrahydrofuran, dioxane and acetic acid, at a temperature of about 0°C. up to the reflux temperature of the system.

The starting materials may be prepared conventionally such as for example, by the following reaction scheme:

$$R_o-CO-CH_3 \rightarrow R_o-\underset{\underset{\displaystyle OH}{|}}{\overset{\overset{\displaystyle CH_3}{|}}{C}}-CN \rightarrow R_o-\underset{\underset{\displaystyle OH}{|}}{\overset{\overset{\displaystyle CH_3}{|}}{C}}-COOH \rightarrow R_o-\overset{\overset{\displaystyle CH_2}{\|}}{C}-COOH$$

7. The reaction $$R_o-\overset{\overset{\displaystyle CH_3}{|}}{CHMgCl} \underset{(Br)}{\overset{CO_2}{\rightarrow}} R_o-\overset{\overset{\displaystyle CH_3}{|}}{CH}-COOH.$$
(I)

The Grignard reagent may be prepared conventionally by reaction of the appropriately substituted alkyl halide with magnesium in the presence of ether; it is then treated in ethereal solution with carbon dioxide and the additive compound so formed is decomposed with acid e.g. dilute sulfuric acid.

8. By means of the Ullmann reaction: i.e.

wherein one of A and B is OH and the other is halogen. Preferably A is OH and B is halogen.

This reaction is normally carried out by heating a metal derivative (e.g. an alkali metal derivative, especially potassium) of the hydroxy compound with the halogen compound (especially an iodo or bromo compound) at 100°–350°C. in the presence of a metal catalyst especially copper powder or copper bronze.

9. Hydrolysis of or an ester thereof, e.g. an alkyl ester, wherein $R_5$ is an acyl group, preferably alkanoyl, most preferably acetyl. Other acyl groups include benzoyl and benzoyl substituted in the phenyl ring, e.g. by halogen, alkyl, alkoxy, nitro, etc. Hydrolysis conditions may be as those described above for method (1).

The starting materials may be prepared by the reaction or an ester thereof, e.g. an alkyl ester.

10. Decarboxylation of

This is conveniently carried out by heating, in the absence or presence of an organic solvent medium. Advantageously it is effected in the presence of a basic organic solvent having a high boiling point e.g. dimethylaniline or quinoline, and preferably at the reflux temperature of the reaction medium.

The starting materials may be prepared by the reaction (or an ester of the propionic acid, e.g. an alkyl ester).

11. Hydrolysis of wherein "alkyl" is preferably methyl. Typical hydrolysis conditions are described under method (1).

The starting materials may be prepared using procedures similar to those described by Meyers and Temple, *J.A.C.S.*, 1970, 92, 6644.

12. Removal of sulfur dioxide from a compound of formula

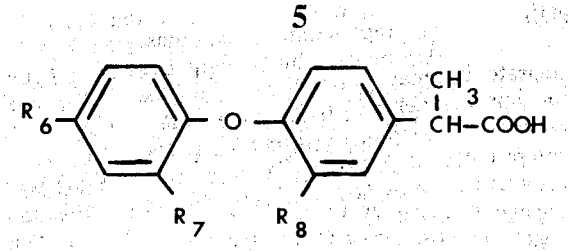

in which at least one of the symbols $R_6$, $R_7$ and $R_8$ is a halosulfonyl group and the remaining symbols correspond to the desired values of $R_1$, $R_2$ or $R_3$, by heating in the presence of a compound useful in decomposing sulfonyl halides. Typical compounds are nickel, platinum, palladium, ruthenium, tris(triphenylphosphine)rhodium chloride, tris(triphenylphosphine)ruthenium dichloride, tetra(triphenyl phosphine)ruthenium dichloride and tris(triphenylphosphine) rhodium fluoride. A temperature of 100°–300°C. is generally used. The reaction may be carried out in the presence of an inert organic solvent, such as benzene or xylene, although the use of a solvent is not necessary.

This reaction is advantageously applicable to the preparation of acids of general formula I wherein $R_1$ is fluorine, $R_2$ is hydrogen, and $R_3$ is halogen or, preferably, hydrogen.

13. Reaction of a compound of formula

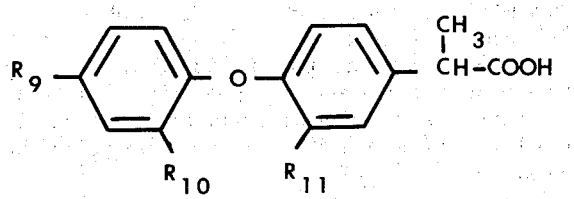

in which at least one of the symbols $R_9$, $R_{10}$, and $R_{11}$ is an amino group and the other symbols correspond to the desired values of $R_1$, $R_2$ or $R_3$ in known manner so as to convert said amino group to the desired halogen atom. Examples of known procedures include the Sandmeyer reaction, wherein the amino compound is diazotized and reacted with a cuprous halide, and the Schiemann reaction wherein the amino compound is diazotized in the presence of a fluorinating agent to form a fluorodiazonium derivative which is then decomposed by heating to give the corresponding fluoro compound. Suitable fluorinating agents include hydrogen fluoride, fluoboric acid, fluosilicic acid and phosphorus pentafluoride.

ESTERS

1. Esterification of the acids by conventional means:

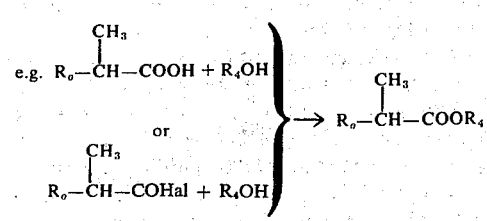

2. Alcoholysis of

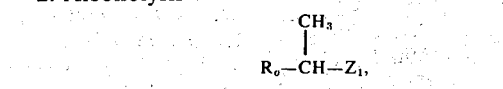

wherein $Z_1$ is cyano, carbamoyl, or N,N-disubstituted thiocarbamoyl (e.g. derived from morpholine).

3. By means of methods (3), (6), (8), (10), (12) and (13) as described under "Acids" but starting with the desired ester in place of the acid.

4. By alcoholysis of the oxazolines described under "Acids (11)".

AMIDES

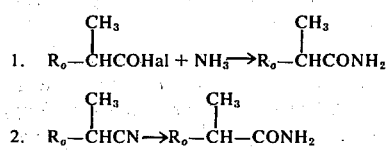

3. Selective hydrolysis of

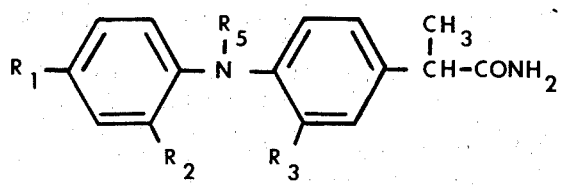

to replace $R_5$ by H. (See "Acids (9)").

4. By means of methods (3), (6), (10), (12) or (13) as described under "Acids" but starting with the amide in place of the acid.

SALTS

1. Reaction of the acids with organic or inorganic bases.
2. Alkaline hydrolysis of

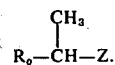

ALCOHOLS

1. Reduction of the acids or, preferably, the esters (especially alkyl esters). The use of lithium aluminium hydride in a suitable solvent e.g. ether, followed by acidification, is one example. Alternatively hydrogenation in the presence of a copper/chromium oxide catalyst may be used. Esters may be reduced with sodium in a lower alkanol.

2. By means of methods (8), (9), (10), (12) or (13) as described under Acids but starting with a protected alcohol in place of the acid. The alcohol may be protected by a conventional readily removable group e.g. benzyl, which is finally removed after the earlier synthesis stages.

The compounds of general formula I possess anti-inflammatory activity and are useful for the treatment of inflammatory conditions. They also possess analgesic and antipyretic properties and are useful for the treatment of conditions of pain and pyretic conditions. They are useful for the treatment of these three conditions individually or in any combination. A particularly notable and important feature of the compounds is their long lasting effect. This feature allows a relatively high blood level to be achieved for a long period following a single dose (as long as about 24 hours in many cases), in contrast to short acting compounds e.g. 2-(4-isobutylphenyl) propionic acid where there is no substantial amount of compound in the blood only a short time following a single dose, e.g. after 3–6 hours in the case of 2-(4-isobutylphenyl) propionic acid. Thus the compounds of the invention in many cases need only be administered once, or sometimes twice, per day, whereas the short acting compounds require to be administered at least three times, and often four times, per day.

The activity of the compounds of the invention has been determined in experimental animals using pharmacological tests which are known to be capable of characterising compounds possessing the therapeutic properties of aspirin, namely anti-inflammatory, analgesic and antipyretic activity; the long lasting effect has been confirmed by blood level experiments.

A preferred group of compounds of the invention are those of general formula I wherein X is oxygen. It is also preferred that at least one of $R_1$, $R_2$ and $R_3$ is a fluorine atom.

A preferred group of compounds of the invention are also those wherein Y is COOH. It is believed that when salts, esters, amides or alcohols derived from these acids are used in place of the acids said derivatives are metabolized by the animal body and are converted in the body into the corresponding acids.

It will be appreciated that, since the compounds of general formula I possess an asymmetric carbon atom, they are ordinarily present in the form of a racemic mixture. The resolution of such racemates may be carried out by any conventional method and the separated optically active stereoisomers form part of the present invention.

The compounds of the invention may be administered in the conventional manner of aspirin or usual manner for other anti-inflammatory, analgesic, and antipyretic agents, for example orally, topically, rectally or parenterally, preferably orally. The optimum dosage rate varies with the route of administration, but normally lies within the range 0.014–14.0 mg./kg./day, more usually between 0.35–7.0 mg./kg./day. The unit dose may vary from 1 mg. to 1000 mg. per subject; for oral administration the dosage rate is preferably 25–500 mg. per subject per day, optionally in divided doses.

In use, the compounds of the invention are administered in conventional formulations and accordingly the invention also provides therapeutic compositions which comprise a compound of the invention in association with pharmaceutical excipients for the production of compositions for oral, topical, rectal or parenteral administration. These compositions preferably contain 0.1–90% by weight of a compound of the invention.

Compositions for oral administration are the preferred compositions of the invention, and these are the conventional pharmaceutical forms for such administration, such a for example tablets, capsules, lozenges, powders, effervescent granules, syrups and aqueous and oily suspensions. The excipients used in the preparation of these compositions are the excipients of the pharmacist's art. Thus in the preparation of tablets, typical excipients include disintegrating agents, e.g., corn starch and lubricating agents, e.g., magnesium stearate; in the preparation of capsules, standard gelatin capsules may be used containing the active ingredient alone or admixed with a diluent. The liquid compositions may comprise as excipients water and sucrose to provide syrups, water, dispersing agents and suspending agents, e.g., sodium carboxymethylcellulose to provide aqueous suspensions, and a non-toxic oil, e.g., a vegetable oil such as arachis oil and a suspending agent to provide oily suspensions.

Compositions for rectal administration are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1–4 carbon atoms which may contain a small proportion of water.

Compositions for parenteral administration are the conventional pharmaceutical forms for such administration, for example sterile suspensions in aqueous or oily media or sterile solutions in propylene glycol.

In some formulations it may be beneficial to use the compounds of the invention in the form of particles of very small size, such as for example, as obtained by fluid energy milling, e.g., micronizing.

The invention further provides a method of treating inflammatory conditions, conditions of pain and pyretic conditions, individually or in any combination, which comprises administering a compound of the invention, preferably orally.

The products of the present invention may of course be employed in combination with other active anti-inflammatory agents, analgesics, and antipyretic agents, or with other drugs, as is already conventional in the art for other existing anti-inflammatory, analgesic and antipyretic materials such as aspirin.

The following non-limitative examples illustrate the invention.

EXAMPLE 1

Ethyl 2-[4-(4-fluorophenoxy)phenyl]-2-methylmalonate (19.6 g.) was refluxed for 1 hour with a mixture of 2.5N aqueous sodium hydroxide (114 ml.) and ethanol (57 ml.). After cooling and acidification with 5N hydrochloric acid, the resulting oil was extracted into ether. The extract was washed with water, dried and the ether distilled. The residue of crude 2-[4-(4-fluorophenoxy)phenyl]-2-methylmalonic acid was decarboxylated by heating for 20 minutes at 220°C. The product was recrystallised several times from benzene/petroleum ether b.p. 62°–68°C. to give 2-[4-(4-fluorophenoxy)phenyl]propionic acid, m.p. 84°–86°C.

The starting material was prepared as follows. An Ullmann reaction using p-fluorophenol and p-bromoacetophenone gave 4'-(4-fluorophenoxy)acetophenone, m.p. 65°–67°C. This was subjected to the Willgerodt reaction using morpholine and sulfur, followed by hydrolysis, to give crude 4-(4-fluorophenoxy)phenylacetic acid, which was esterified and gave ethyl 4-(4-fluorophenoxy)phenylacetate, b.p. 139°–142°C./0.3 mm. This ester was treated conventionally with diethyl carbonate and sodium ethoxide, and then with dimethyl sulfate, to yield the required ethyl 2-[4-(4-fluorophenoxy)phenyl]-2-methylmalonate, b.p. 174°–182°C./0.7 mm.

EXAMPLE 2

Ethyl 2-[4-(4-chlorophenoxy)phenyl]-2-methylmalonate (b.p. 186°–187°c./0.3 mm.) was treated by the procedure of Example 1 to yield 2-[4-(4-chlorophenoxy)phenyl]propionic acid, m.p. 105°–107°C.

The starting material was prepared by the procedures of Example 1 from 4'-(4-chlorophenoxy)acetophenone (C.A., 62, 14581) via ethyl 4-(4-chlorophenoxy)phenylacetate, b.p. 167°–168°c./0.4 mm.

EXAMPLE 3

Potassium hydroxide (3.4 g.) was fused at 180°C. with water (1 ml.), and 2,4-difluorophenol (5.2 g.) added. 2-(4-Iodophenyl)propionic acid (5.5 g.) and copper bronze (0.2 g.) were then added to the melt, and the resulting mixture was stirred at 160°–170°C. for 2 hours. The cooled solid was extracted with methylene chloride containing a little dilute hydrochloric acid, filtered, and the solution extracted with dilute potassium carbonate solution. The aqueous extract was washed with ether and acidified with dilute hydrochloric acid; the resulting oil was isolated in ether and evaporated to dryness. The resulting solid was purified by preparative layer chromatography using 5% acetic acid/petroleum ether b.p. 62°–68°C. and eluting with ethyl acetate; recrystallization from petroleum ether b.p. 80°–100°C. gave 2-[4-(2,4-difluorophenoxy)-phenyl]propionic acid, m.p. 105°–106°C.

EXAMPLE 4

The following compounds were prepared by the Ullmann reaction in a similar manner to that described in Example 3.

2-[4-(2,4-dichlorophenoxy)phenyl]propionic acid, m.p. 77°–80°C.

2-[4-(4-chloro-2-fluorophenoxy)phenyl]propionic acid, m.p. 80°–83°C.

2-[4-(4-fluorophenoxy)phenyl]propionic acid, m.p. 84°–86°C.

EXAMPLE 5

Methyl 2-(4-iodophenyl)propionate (2 g.), acet-p-chloroanilide (1.17 g.), potassium carbonate (0.62 g.) and copper powder (0.1 g.) were heated at 165°C. for 7.5 hours. The cooled solid was triturated with methylene chloride, filtered, and the filtrate evaporated to dryness. The residue was refluxed for 1.5 hours with ethanol (7 ml.) and 2.5N sodium hydroxide (14 ml.); ethanol was distilled in vacuo and the residue diluted with water, washed with ether and acidified with dilute hydrochloric acid. The resulting oil was isolated in ether and evaporated to dryness. The resulting gum was purified by preparative layer chromatography using 5% acetic acid/petroleum ether b.p. 62°–68°C. and eluting with ethyl acetate; recrystallization from benzene/petroleum ether b.p. 62°–68°C. and from petroleum ether b.p. 80°–100°C. gave 2-[4-(4-chloroanilino)-phenyl]propionic acid, m.p. 106-109°C.

In a similar manner there were prepared:

2-[4-(4-fluoroanilino)phenyl]propionic acid, m.p. 105°–108°C.

2-[4-(2,4-difluoroanilino)phenyl]propionic acid, m.p. 86°–87°C.

EXAMPLE 6

Ethyl 3-chloro-4-(4-fluorophenoxy)phenyl-2-methylmalonate (b.p. 198°–202°C./1.2 mm.) was treated by the procedure of Example 1 to yield 2-[3-chloro-4-(4-fluorophenoxy)phenyl]propionic acid, m.p. 59°–61°C.

The starting material was prepared by the procedures of Example 1 from p-fluorophenol and 4'-bromo-3'-nitroacetophenone via 4'-(4-fluorophenoxy)-3'-nitroacetophenone, m.p. 96°–98°C., 3'-amino-4'-(4-fluorophenoxy)acetophenone, m.p. 83°–85°C., 3'-chloro-4'-(4-fluorophenoxy)acetophenone, m.p. 68°–70°C. and ethyl 3-chloro-4-(4-fluorophenoxy)phenylacetate, b.p. 171°–174°C./0.8 mm. 4'-Bromo-3'-nitroacetophenone m.p. 114°–116°C. was prepared by nitration of 4'-bromoacetophenone.

EXAMPLE 7

2-[4-(4-fluorophenoxy)phenyl]propionic acid (2.32 g.) in ethanol (16 ml.) containing concentrated sulfuric acid (0.5 ml.) were refluxed for 5 hours and the alcohol removed. After dilution with water the product was isolated in ether and distilled to give ethyl 2-[4-(4-fluorophenoxy)phenyl]propionate, b.p.169°–171°C./2 mm.

Example 8

Ethyl 2-[4-(4-fluorophenoxy)phenyl]propionate (1.3 g.) in dry ether (5 ml.) was added dropwise to lithium aluminium hydride (200 mg.) in dry ether (5 ml.). After refluxing for 1 hour the excess hydride was decomposed with dilute sulfuric acid, and the ether layer was distilled to give 2-[4-(4-fluorophenoxy)-phenyl]propanol, b.p. 151°–152°C./0.6 mm.

EXAMPLE 9

A mixture of 2-[4-(2,4-difluorophenoxy)phenyl]propionic acid (2 g.) and thionyl chloride (10 ml.) was refluxed for 10 minutes. Excess thionyl chloride was distilled and the residue in ether (10 ml.) was added dropwise to ammonium hydroxide (S.G. 0.88, 20 ml.) cooled in ice. After 15 minutes the ether layer was separated and evaporated. The resulting solid was purified by preparative layer chromatography using 5% acetic acid/toluene and eluting with ethyl acetate; recrystallization from petroleum ether b.p. 100°–120°C. gave 2-[4-(2,4-difluorophenoxy)phenyl]propionamide, m.p. 107°–110°C.

EXAMPLE 10

By the methods hereinbefore described, the following compounds are obtained (and salts, esters, amides or alcohols derived therefrom):

2-[3-fluoro-4-(4-fluorophenoxy)phenyl]propionic acid

2-[4-(2-chloro-4-fluorophenoxy)phenyl]propionic acid

2-[4-(2-bromo-4-fluorophenoxy)phenyl]propionic acid

2-[3-bromo-4-(4-fluorophenoxy)phenyl]propionic acid

2-[3-chloro-4-(4-chlorophenoxy)phenyl]propionic acid

2-[4-(4-chlorophenoxy)-3-fluorophenyl]propionic acid

2-[4-(2-bromo-4-chlorophenoxy)phenyl]propionic acid

2-[3-bromo-4-(4-chlorophenoxy)phenyl]propionic acid
2-[4-(4-bromophenoxy)phenyl]propionic acid
2-[4-(2,4-dibromophenoxy)phenyl]propionic acid
2-[3-bromo-4-(4-bromophenoxy)phenyl]propionic acid
2-[4-(4-bromo-2-fluorophenoxy)phenyl]propionic acid
2-[4-(4-bromophenoxy)-3-fluorophenyl]propionic acid
2-[4-(4-bromo-2-chlorophenoxy)phenyl]propionic acid
2-[4-(4-bromophenoxy)-3-chlorophenyl]propionic acid
2-[4-(2,4-dichloroanilino)phenyl]propionic acid
2-[3-fluoro-4-(4-fluoroanilino)phenyl]propionic acid
2-[4-(4-bromoanilino)phenyl]propionic acid
2[4-(4-bromo-2-fluoroanilino)phenyl]propionic acid
2-[4-(4-bromoanilino)-3-fluorophenyl]propionic acid
2-[4-(4-chloro-2-fluoroanilino)phenyl]propionic acid
2-[4-(4-chloroanilino)-3-fluorophenyl]propionic acid
(+) 2-[4-(4-fluorophenoxy)phenyl]propionic acid
(−)-2-[4-(4-fluorophenoxy)phenyl]propionic acid
(+)-2-[4-(2,4-difluorophenoxy)phenyl]propionic acid
(−)-2-[4-(2,4-difluorophenoxy)phenyl]propionic acid

EXAMPLE 11

2-[4-(4-Chlorophenoxy)phenyl]propionic acid (740 mg.) and benzylamine (300 mg.) were mixed in ether. The precipitated solid was recrystallized from alcohol/ether to give the benzylamine salt of 2-[4-(4-chlorophenoxy)phenyl]propionic acid, m.p. 138°–139°C.

EXAMPLE 12

No. 5 hard gelatin capsules were prepared each containing the following:

| (a) | 2-[4-(4-fluorophenoxy)phenyl]propionic acid | | 5 mg. |
| | lactose | | 95 mg. |
| (b) | 2-[4-(4-fluorophenoxy)phenyl]propionic acid | | 5 mg. |
| | calcium phosphate | | 5 mg. |
| | corn starch | | 90 mg. |
| (c) | 2-[4-(4-fluorophenoxy)phenyl]propionic acid | | 5 mg. |
| | corn starch | | |
| | lactose | equal parts by weight | 95 mg. |
| | calcium phosphate | | |

EXAMPLE 13

The following mixture (parts by weight) was formed into tablets in conventional manner, each tablet containing 5 mg. of active ingredient

| 2-[4-(4-fluorophenoxy)phenyl]propionic acid | 5 |
| --- | --- |
| corn starch | 30 |
| lactose | 163 |
| stearic acid | 1 |
| magnesium stearate | 1 |

Compositions similar to those described in Examples 12 and 13 were prepared containing as active ingredient other compounds of the invention described in Examples 1 – 11.

We claim:
1. A compound of the formula

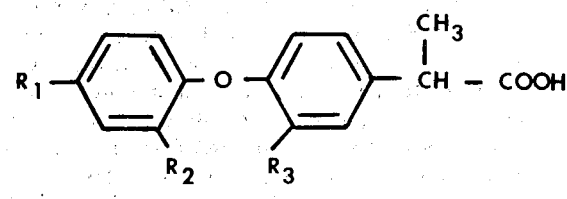

in which $R_1$ is halogen; $R_2$ and $R_3$ are each selected from the group consisting of hydrogen and halogen, with the proviso that at least one of $R_2$ and $R_3$ is hydrogen; together with the pharmaceutically acceptable lower alkyl esters, inorganic salts and organic salts thereof.

2. A compound as claimed in claim 1 wherein at least one of $R_1$, $R_2$ and $R_3$ is a fluorine atom.

3. A 2-[4-(4-fluorophenoxy)phenyl]propionic acid; together with the pharmaceutically acceptable lower alkyl esters, inorganic salts and organic salts thereof.

4. A 2-[4-(2,4-difluorophenoxy)phenyl]propionic acid; together with the pharmaceutically acceptable lower alkyl esters, inorganic salts and organic salts thereof.

5. A 2-[4-(4-chlorophenoxy)phenyl]propionic acid; together with the pharmaceutically acceptable lower alkyl esters, inorganic salts and organic salts thereof.

6. A 2-[3-bromo-4-(4-fluorophenoxy)phenyl]propionic acid; together with the pharmaceutically acceptable lower alkyl esters, inorganic salts and organic salts thereof.

* * * * *